United States Patent [19]

Ritchart et al.

[11] Patent Number: 4,738,265
[45] Date of Patent: Apr. 19, 1988

[54] DUAL STOP COCK

[75] Inventors: Mark A. Ritchart, Orange; Leo J. Brueggeman, Huntington Beach, both of Calif.

[73] Assignee: Baxter Travenol Laboratories, Inc., Deerfield, Ill.

[21] Appl. No.: 31,872

[22] Filed: Mar. 30, 1987

[51] Int. Cl.$^4$ .............................................. A61B 5/02
[52] U.S. Cl. ................................... 128/673; 128/748; 137/625.43; 251/208
[58] Field of Search .................. 128/672, 673–675, 128/748; 137/625.15, 0.42–0.43; 251/208

[56] References Cited

U.S. PATENT DOCUMENTS

| | | |
|---|---|---|
| 540,215 | 4/1895 | McElroy . |
| 868,772 | 3/1907 | Gold . |
| 1,554,712 | 10/1979 | Cooper . |
| 1,932,976 | 10/1933 | Lamb et al. ............... 137/625.43 |
| 3,157,201 | 11/1964 | Littmann ............... 137/625.47 |
| 3,418,853 | 12/1968 | Curtis ............... 128/675 X |
| 3,610,228 | 10/1971 | Temkin . |
| 3,618,637 | 11/1971 | Santomieri . |
| 3,678,960 | 7/1972 | Leibinsohn . |
| 3,783,900 | 1/1974 | Waldbillig . |
| 3,834,372 | 10/1974 | Turney . |
| 4,003,403 | 1/1977 | Nehring . |
| 4,055,232 | 10/1977 | Moore . |
| 4,207,923 | 6/1980 | Giurtino . |
| 4,508,103 | 4/1985 | Calisi . |
| 4,509,946 | 4/1985 | McFarlane . |
| 4,543,996 | 10/1985 | Baron . |
| 4,566,480 | 1/1986 | Parham . |
| 4,648,868 | 3/1987 | Hardwick et al. ............... 128/675 X |

FOREIGN PATENT DOCUMENTS 2313363  9/1974  Fed. Rep. of Germany ...... 128/672

Primary Examiner—Kyle L. Howell
Assistant Examiner—Angela D. Sykes
Attorney, Agent, or Firm—Gordon L. Peterson

[57] ABSTRACT

A system for measuring first and second fluid pressures within a patient comprising a valve having first and second positions, first and second conduits for providing communication between a fluid source and the valve, a pressure transducer coupled to the first conduit upstream of the valve, and third and fourth conduits for providing communication between the valve and first and second fluid pressures, respectively. When the valve is in the first position, it couples the first conduit to the third conduit, and the second conduit to the fourth conduit so that the pressure transducer can measure the first fluid pressure. When the valve is in the second position, it couples the first conduit to the fourth conduit and the second conduit to the third conduit so that the pressure transducer can measure the second fluid pressure. In both positions of the valve, fluid flows through the transducer.

13 Claims, 2 Drawing Sheets

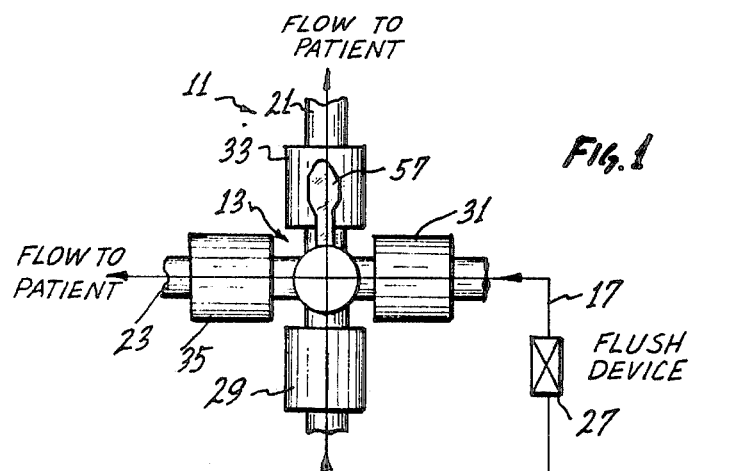
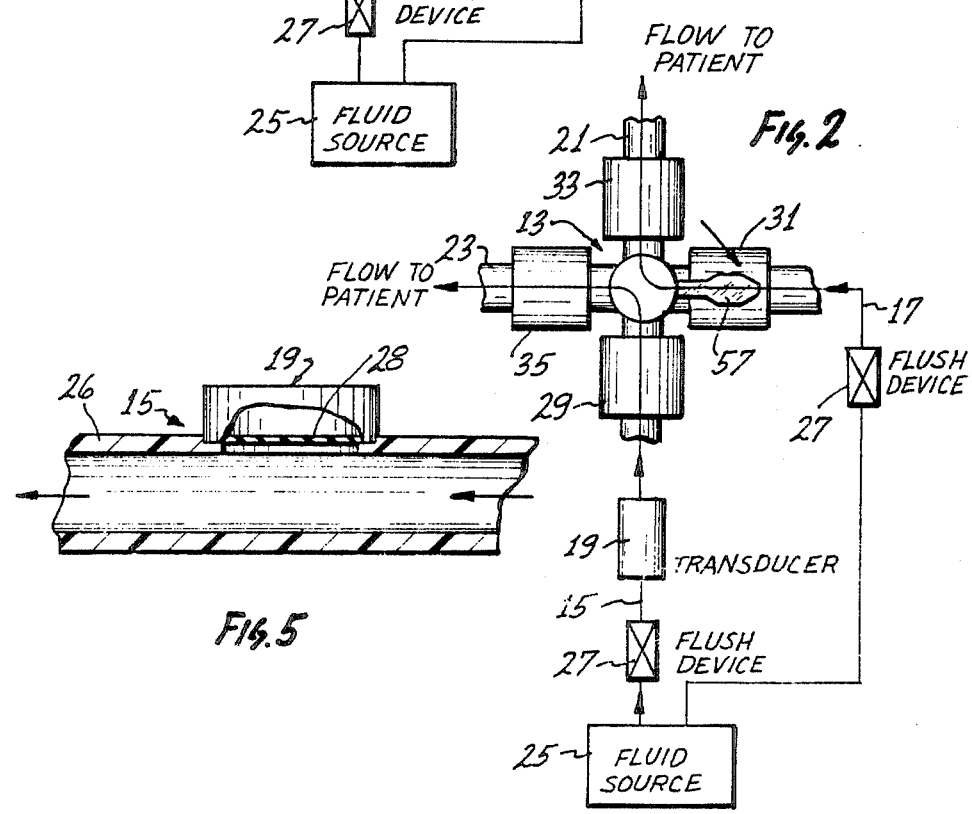

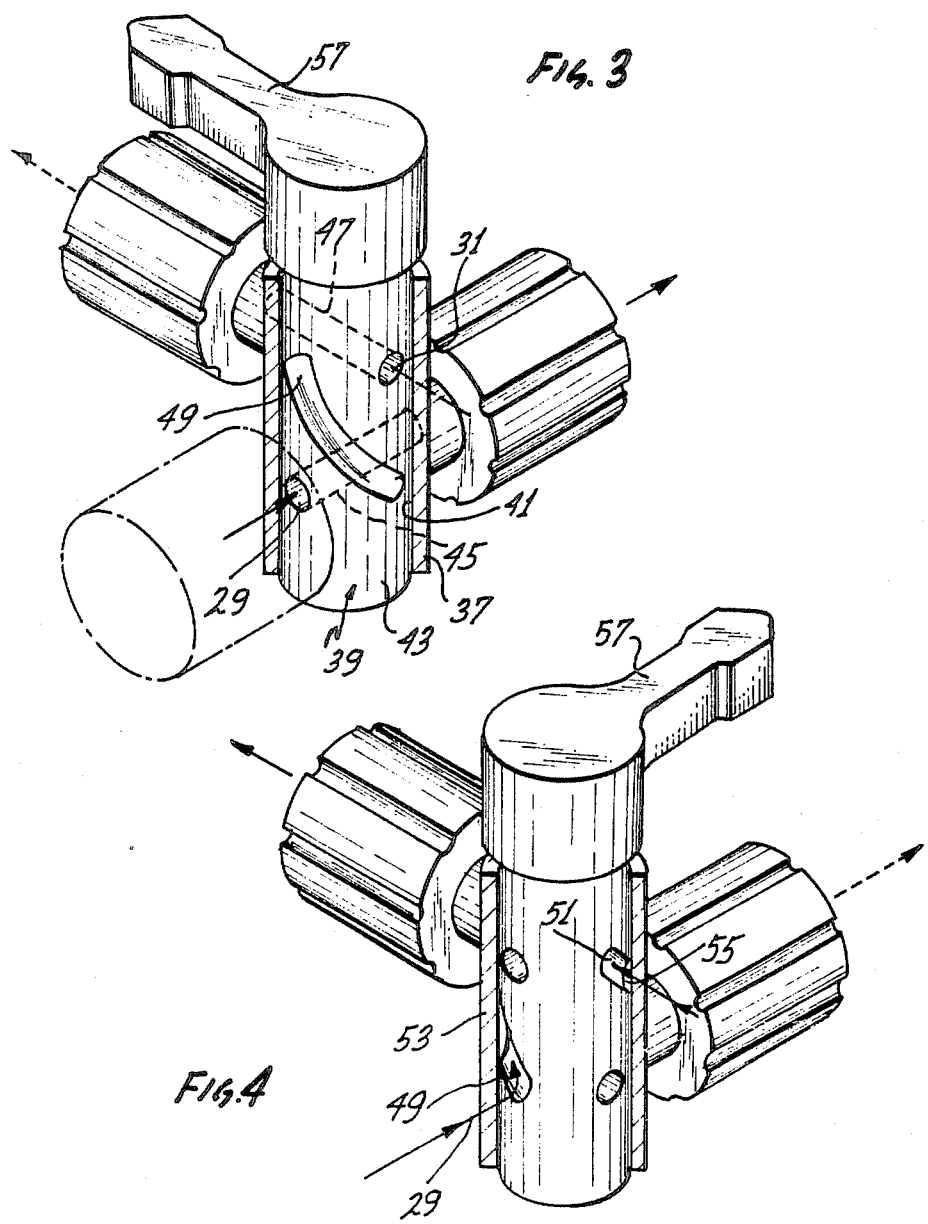

DUAL STOP COCK

BACKGROUND OF THE INVENTION

It is sometimes necessary or desirable to invasively monitor the blood pressure of a patient at two locations within the cardiovascular system. When this is done, it is necessary to provide continuous flow of an appropriate solution, such as a saline solution, to both locations to keep the conduits patent.

To reduce the cost of the pressure-measuring system, a single pressure transducer can be used to measure the pressure at both locations. This is accomplished by a suitable switching system which switches the transducer from one circuit to the other as may be required so that the pressure at the two locations can be sequentially measured.

Although this is a sound concept, prior art systems implementing this concept have certain disadvantages. For example, in some systems of this type, there is no flow of the solution through the transducer, i.e., the transducer is in a deadend path. It is believed that this increases the likelihood of problems with infection. In another system of this type, flow through the transducer is provided. However, in this latter system, the flow of solution to one of the locations is shut off when the transducer is switched to monitor the pressure at another of the locations. Thus, problems with patency of the lines is more likely to develop. Accordingly, neither of these systems provides both flow through the transducer and continuous flow of solution through both lines leading to the patient, regardless of which pressure is being monitored.

SUMMARY OF THE INVENTION

This invention provides a system for measuring first and second fluid pressures within a patient which overcomes the disadvantages noted above. With this invention, there is both flow past the pressure transducer and continuous flow of solution through both conduits leading to the patient regardless of which pressure is being monitored. Although this invention is particularly adapted for the invasive monitoring of the blood pressure of a patient at two locations within the cardiovascular system, it is more generally applicable to the measurement of first and second fluid pressures within the patient.

The system of this invention may include a valve having first and second positions, first and second conduits for providing communication between a fluid source and the valve, a pressure transducer and third and fourth conduits for providing communication between the valve and the first and second fluid pressures, respectively, within the patient. To provide for continuous flow of solution past the transducer, it is coupled to the first conduit upstream of the valve. Accordingly, the flow of solution from the fluid source through the first conduit flows past the pressure transducer such that there is no deadend flow to the transducer.

The valve enables the transducer to selectively measure the pressure in either the third or fourth conduit while continuously providing for the flow of solution from the fluid source through the third and fourth conduits to the patient. Accordingly, the valve enables the pressure transducer to sequentially perform two pressure-measurement functions while assuring that the third and fourth conduits leading to the patient remain patent.

To accomplish this, the valve is a four-way valve which preferably includes means responsive to the valve being in the first position for coupling the first conduit to the third conduit, and the second conduit to the fourth conduit so that the pressure transducer can measure the first fluid pressure, i.e., the pressure in communication with the third conduit. The valve also includes means responsive to the valve being in the second position for coupling the first conduit to the fourth conduit and the second conduit to the third conduit so that the pressure transducer can measure the second fluid pressure, i.e., the fluid pressure transmitted by the fourth conduit. In both positions of the valve, solution from the fluid source is transmitted through the valve and the third and fourth conduits to the patient to keep these conduits patent.

The flow of solution from the fluid source can be at whatever rate is considered appropriate under the circumstances. Preferably, a flush valve is provided in one or both of the first and second conduits. The flush valve has a normal position in which a relatively low flow passes through the flush valve, and a flush position in which a higher flushing flow can pass through the flush valve.

As applied to the system, the valve can be of various different constructions so long as the necessary valve functions are carried out. However, this invention also provides a novel and advantageous four-way valve or dual flow stop cock which provides two inlets and permits a selection between two outlets while keeping the size of the valve small. The valve ca be inexpensively constructed of plastic and is disposable. Although this valve is particularly adapted for use in the system of this invention, it can be used in various different environments, within and without the medical field, where its particular functions are desired.

The valve includes a valve housing having first, second, third and fourth ports and a valve element mounted in the valve housing for movement between the first and second positions. The valve has first and second passages for providing communication in the first position of the valve between the first and third ports and the second and fourth ports, respectively. The valve also has third and fourth passages, respectively. The third and fourth passages provide communication in the second position between the first and fourth ports and the second and third ports, respectively.

In a preferred construction, the valve element is mounted in the valve housing for movement about a rotational axis between the first and second positions, and the first and second passages extend through the valve element. The valve element also has first and second grooves in its peripheral surface which cooperate with the housing to define the third and fourth passages, respectively. To facilitate manufacture, the first and third ports preferably are spaced along the rotational axis from the second and fourth ports, and the first and second passages extend diametrically through the valve element along different diametral lines. To facilitate operation of the valve, the ports are preferably substantially spaced circumferentially.

The invention, together with additional features and advantages thereof, may best be understood by reference to the following description taken in connection with the accompanying illustrative drawing.

BRIEF DESCRIPTION OF THE DRAWING

FIG. 1 is a schematic illustration of a pressure-measuring system constructed in accordance with the teachings of this invention, with the valve being in a first position.

FIG. 2 is a schematic illustration similar to FIG. 1, with the valve being in the second position.

FIG. 3 is an isometric view with parts broken away of a preferred valve, with the valve being in the first position.

FIG. 4 is a view similar to FIG. 3, with the valve being in the second position.

FIG. 5 is a fragmentary sectional view illustrating one way in which fluid from the fluid source can flow through the transducer.

DESCRIPTION OF THE PREFERRED EMBODIMENT

FIG. 1 shows a pressure-measuring system 11 which generally comprises a valve 13, inlet conduits 15 and 17, a pressure transducer 19 and outlet conduits 21 and 23. The inlet conduits 15 and 17 provide communication between a fluid source 25 and the valve 13 so that fluid from the fluid source can be transmitted to the valve. The fluid in the fluid source 25 is of the type suitable for keeping a conduit leading to a patient patent and may be, for example, a saline solution or heparin solution. The fluid source 25 may be a single source as indicated in FIGS. 1 and 2, or if desired, it may include separate sources for the inlet conduits 15 and 17, respectively.

The pressure transducer 19 may be of any conventional type suitable for measuring a patient's blood pressure. The transducer 19 is coupled directly into the conduit 15 (FIGS. 1, 2 and 5) so that the fluid flows past the transducer. As shown in FIG. 5, the transducer 19 may be mounted on a flow-through housing 26, which forms a portion of the conduit 15, and have a pressure responsive diaphragm 28 exposed to the fluid flowing through the flow-through housing so that the diaphragm will deflect in accordance with the pressure of the fluid flowing through the conduit 15. The pressure transducer 19 responds to the deflections of the diaphragm 28 in a known manner to provide a pressure signal indicative of the pressure of the fluid in the conduit 15. As shown most clearly in FIG. 5, the transducer 19 is not in a deadend flow path but rather is located in a flow-through flow path so that the fluid in the conduit 15 flows past or through the transducer 19.

Identical flush devices 27 are preferably provided in each of the inlet conduits 15 and 17. Each of the flush devices or flush valves may be of conventional construction and have a normal position in which a relatively low flow of fluid can pass through the flush valve and a flush position in which a higher flushing flow can pass through the flush valve. The flush valve is normally releasably retained in the normal position and can be manually manipulated to provide for flushing flow as may be considered desirable by the attendant.

The valve 13 has inlet ports 29 and 31 coupled to the inlet conduits 15 and 17, respectively, and outlet ports 33 and 35 coupled to the outlet conduits 21 and 23, respectively. The outlet conduits 21 and 23 lead to two different locations within the vascular system of a patient. For example, each of the conduits 21 and 23 may terminate in, or include, a needle or catheter in the venous or arterial sides of the cardiovascular system. Alternatively, the outlet conduits 21 and 23 may include, or terminate in, two different lumens of a single catheter which are exposed to the two locations of the cardiovascular system where blood pressure is to be monitored.

The valve 13 has at least two positions. In the first position, the valve 13 couples the inlet conduits 15 and 17 to the outlet conduits 21 and 23, respectively, while blocking communication through the valve between the inlet conduit 15 and the outlet conduit 23 and between the inlet conduit 17 and the outlet conduit 21. Accordingly, in the first position of the valve, the pressure transducer is exposed to, and can measure, the pressure in the outlet conduit 21, which is essentially the same as the pressure at the location of the cardiovascular system to which the outlet conduit 21 is coupled. In addition, there is continuous fluid flow from the fluid source 25 through both of the outlet conduits 21 and 23 to the patient to keep these conduits patent. The flush devices 27 can be operated to momentarily increase the rate of fluid flow from the fluid source 25 to the patient.

The valve 13 has a second position (FIG. 2) in which the inlet conduits 15 and 17 are coupled to the outlet conduits 23 and 21, respectively. In the second position, the valve 13 blocks communication through the valve between the inlet conduit 15 and the outlet conduit 21 and between the inlet conduit 17 and the outlet conduit 23. In both positions of the valve, the valve blocks flow through the valve between the inlet conduits 15 and 17 and between the outlet conduits 21 and 23.

In the second position of the valve 13, the transducer 19 is exposed to, and can measure, the pressure of the fluid in the outlet conduit 23 and, hence, the pressure of the blood at the location to which the conduit 23 is exposed. In the second position, there is also a continuous flow of solution from the fluid source 25 through both of the outlet conduits 21 and 23 to the patient. In use of the system 11, the transducer 19 may be used, for example, to normally monitor the pressure in the outlet conduit 21 and to be occasionally momentarily switched to the position of FIG. 2 to obtain a pressure reading applicable to the outlet conduit 23 and the associated location within the cardiovascular system.

FIGS. 3 and 4 show a preferred form of the valve 13, which may be used in the system of FIGS. 1 and 2 or elsewhere. The valve of FIGS. 3 and 4 may be incorporated into the system of FIGS. 1 and 2 by connecting the ports 29, 31, 33 and 35 to the conduits 15, 17, 23 and 25 as shown in FIGS. 1 and 2. The valve 13 includes a valve housing 37 having the inlet ports 29 and 31 and the outlet ports 33 and 35 thereon. A valve element 39 is rotatably mounted in the valve housing 37 for rotation about a rotational axis between a first position (FIGS. 1 and 3) and a second position (FIGS. 2 and 4). Thus, the first and second positions of the valve 13 are in this embodiment, the first and second positions, respectively, of the valve element 39. The valve 13 may be constructed of any suitable material, such as a suitable molded plastic material.

The valve housing 37 has a cylindrical bore 41, and the valve element 39, in this embodiment, has a cylindrical peripheral surface 43 and is mounted in the bore 41. The valve element 39 has passages 45 and 47 extending through the valve element to provide communication between the inlet port 29 and the outlet port 33 and between the inlet port 31 and the outlet port 35 when the valve is in the first position of FIG. 3. In the position of FIG. 3, the valve element 39 blocks communication through the valve element between all of the other ports.

The valve element 39 also has helical grooves 49 and 51 in the peripheral surface 43 which cooperate with the valve housing 37 to define helical passages 53 and 55, respectively. In the first position of the valve element (FIG. 3), the passages 53 and 55 connect none of the ports. However, in the second position of the valve 13 (FIG. 4), the passages 53 and 55 provide communication between the inlet port 29 and the outlet port 35 and between the inlet port 31 and the outlet port 33. In the position of FIG. 4, communication between all of the other ports is blocked.

In a preferred construction, the ports 29 and 33 are diametrically opposed and so are the ports 31 and 35. The passages 45 and 47 extend diametrically through the valve element 39 and are displaced 90 degrees from each other. In addition, the ports 31 and 35 and the passage 47 are spaced along the rotational axis from the ports 29 and 33 and the passage 45. The ports 29, 31, 33, and 35 are equally spaced circumferentially and, in this embodiment, are spaced circumferentially by 90 degrees. The grooves 49 and 51 extend for about 90 degrees circumferentially and for a sufficient distance axially to join the ports 29 and 35 and the ports 31 and 33, respectively.

A valve handle 57 is suitably coupled to the valve element 39 to permit the valve element 39 to be manually rotated 90 degrees between the positions of FIGS. 3 and 4. The valve element 39 is mounted for rotation in the valve housing 37 in any suitable conventional manner, and stops (not shown) may be provided, if desired, to block counterclockwise rotation of the valve element 39 beyond the position shown in FIG. 3 and to block clockwise rotation of the valve element beyond the position shown in FIG. 4.

Although an exemplary embodiment of the invention has been shown and described, many changes, modifications and substitutions may be made by one having ordinary skill in the art without necessarily departing from the spirit and scope of this invention.

We claim:

1. A system for measuring first and second fluid pressures within a patient comprising:
   a valve having first and second positions;
   first and second conduits for providing communication between a fluid source and the valve;
   a pressure transducer coupled to the first conduit upstream of the valve so that fluid in the first conduit can flow past the transducer;
   third and fourth conduits for providing communication between the valve and the first and second fluid pressures, respectively, within the patient;
   said valve including means responsive to the valve being in said first position for coupling the first conduit to the third conduit and the second conduit to the fourth conduit while blocking communication through the valve between the first and fourth conduits and between the second and third conduits whereby the pressure transducer can measure the first fluid pressure and fluid from the fluid source can flow past the transducer and the third and fourth conduits to the patient; and
   said valve including means responsive to the valve being in said second position for coupling the first conduit to the fourth conduit and the second conduit to the third conduit while blocking communication through the valve between the first and third conduits and between the second and fourth conduits whereby the pressure transducer can measure the second fluid pressure and fluid from the fluid source can flow past the transducer and the third and fourth conduits to the patient.

2. A system as defined in claim 1 including a flush valve in at least one of the first and second conduits having a normal position in which a relatively low flow can pass through the flush valve and a flush position in which a higher flushing flow can pass through the flush valve, said flush valve including means for releasably retaining the flush valve in said normal position.

3. A system as defined in claim 1 wherein said valve includes a valve housing having first, second, third and fourth ports coupled, respectively, to the first, second, third and fourth conduits and a valve element rotatably mounted in said valve housing for rotation about a rotational axis between said first and second positions.

4. A system as defined in claim 3 wherein said valve element has first and second passages extending through the valve element to provide communication in said first position between the first and third ports and the second and fourth ports, respectively, while blocking communication through the valve between the first port and the second port, the first port and the fourth port, and the second and third ports.

5. A system as defined in claim 4 wherein said first and third ports are diametrically opposed and said first passage extends diametrically through the valve element.

6. A system as defined in claim 3 wherein said valve element has a peripheral surface and first and second grooves in said peripheral surface which cooperate with said housing to define third and fourth passages, respectively.

7. A system as defined in claim 3 wherein said first and third ports are spaced along the rotational axis from the second and fourth ports 8. A valve comprising:
   a valve housing having first, second, third and fourth ports;
   a valve element rotatably mounted in said valve housing for rotation about a rotational axis between first and second positions;
   said valve element having first and second passages extending through the valve element to provide communication in said first position between the first and third ports and the second and fourth ports, respectively, said valve element in said first position blocking communication through the valve between the first port and the second port, the first port and the fourth port, and between the second and third ports, said first and second passages providing essentially no communication in said second position among said first, second, third and fourth ports;
   said valve element having a peripheral surface and first and second grooves in said peripheral surface which cooperate with said housing to define third and fourth passages, respectively; and
   said third and fourth passages providing communication in said second position between the first and fourth ports and the second and third ports, respectively, said valve element in said second position blocking communication between the first port and the third port, the first port and the second port, and between the second port and the fourth port, said third and fourth passages providing no communication in said first position among said first, second, third or fourth ports.

9. A system as defined in claim 8 wherein said first and third ports are spaced along the rotational axis from the second and fourth ports.

10. A system as defined in claim 9 wherein said first and third ports and said second and fourth ports are diametrically opposed along different diametral lines.

11. A system as defined in claim 8 wherein said first and third ports are diametrically opposed and said first passage extends diametrically through the valve element.

12. A system as defined in claim 8 wherein said first, second, third and fourth ports are substantially equally spaced circumferentially.

13. A valve comprising:
a valve housing having first, second, third and fourth ports;
a valve element mounted in said valve housing for movement between first and second positions;
first means for providing first and second passages which provide communication in said first position between the first and third ports and the second and fourth ports, respectively, said valve element in said first position blocking communication through the valve between the first port and the second port, the first port and the fourth port, and between the second and third ports, said first and second passages providing essentially no communication in said second position among said first, second, third and fourth ports; and
second means for providing third and fourth passages which provide communication in said second position between the first and fourth ports and the second and third ports, respectively, said valve element in said second position blocking communication between the first port and the third port, the first port and the second port, and between the second port and the fourth port, said third and fourth passages providing no communication in said first position among said first, second, third or fourth ports.

* * * * *